United States Patent [19]

Kirby et al.

[11] Patent Number: 4,699,790

[45] Date of Patent: Oct. 13, 1987

[54] ANTIBIOTIC LL-C19004

[75] Inventors: Jane P. Kirby, New City; Donald B. Borders, Suffern; May D. Lee, Monsey, all of N.Y.; William M. Maiese, Bridgewater; Raymond T. Testa, Cedar Groove, both of N.J.; David P. Labeda, Peoria, Ill.

[73] Assignee: American Cyanamid Company, Stamford, Conn.

[21] Appl. No.: 775,901

[22] Filed: Sep. 13, 1985

Related U.S. Application Data

[63] Continuation-in-part of Ser. No. 624,449, Jun. 25, 1984, abandoned.

[51] Int. Cl.$^4$ .......................... A61K 35/72; C12P 1/02
[52] U.S. Cl. ...................................... 424/117; 435/171
[58] Field of Search ......................... 424/117; 435/171

Primary Examiner—Jerome D. Goldberg
Attorney, Agent, or Firm—Mary-Ellen M. Timbers

[57] ABSTRACT

A new antibacterial agent designated LL-C19004 is described, which antibacterial agent is produced through microbiological fermentation, under controlled conditions using a new species of Saccharothrix, *Saccharothrix espanaensis* (NRRL 15764).

4 Claims, 4 Drawing Figures

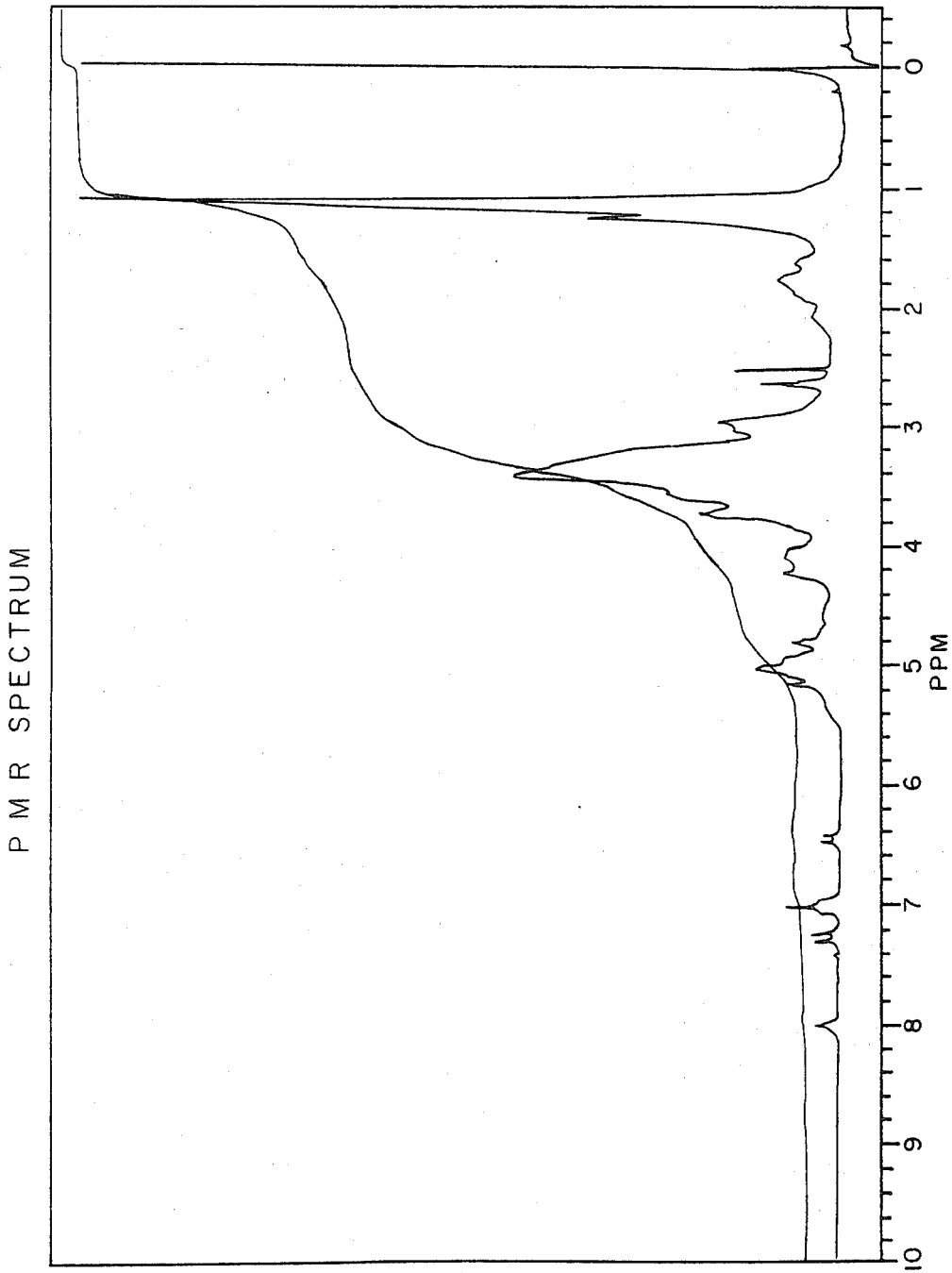

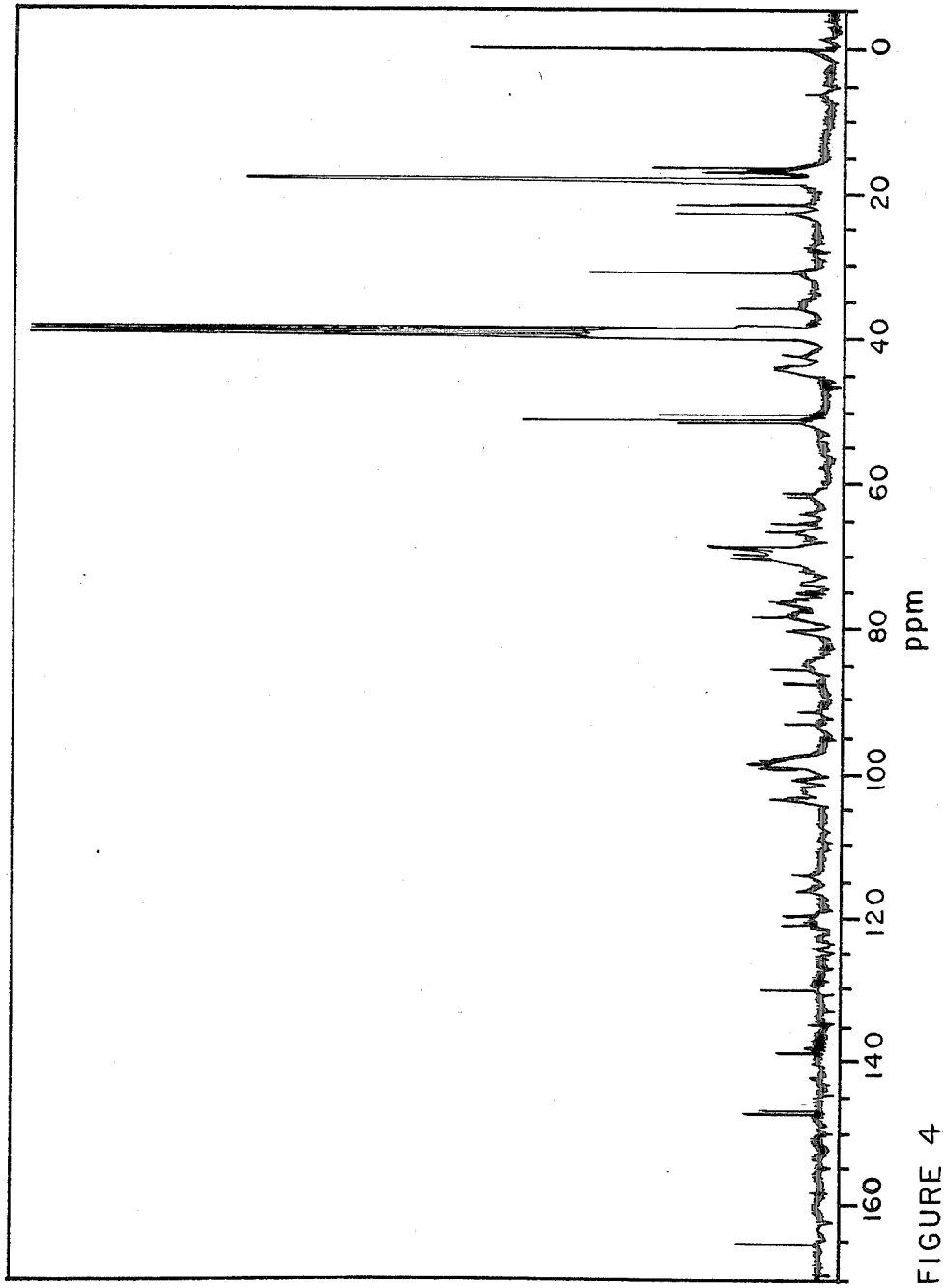

ANTIBIOTIC LL-C19004

BRIEF SUMMARY OF THE INVENTION

This application is a continuation-in-part of application Ser. No. 624,449 filed June 25, 1984, now abandoned.

This invention relates to a new antibacterial agent designated LL-C19004, to its production by fermentation, to methods for its recovery and concentration from crude solutions and to processes for its purification. The present invention includes within its scope the antibacterial agent in dilute form, as a crude concentrate and in pure form. The effects of this new agent on specific microorganisms, together with its chemical and physical properties, differentiate it from previously described, antibacterial agents.

The structure of LL-C19004 is unknown at the present time. However, the antibiotic appears to be weakly basic polysaccharide containing a chromophoric group.

The physiochemical characteristics of antibiotic LL-C19004 are as follows:

(a) Typical elemental analysis (aproximate): C, 45.14; H, 6.48; N, 4.16; S, 1.70; O, 34.90; ash, 7.1.
(b) Ultraviolet absorption spectra, as shown in FIG. I: $\lambda_{max}^{H2O}$nM($E_1\ _{cm}^{1\%}$) 214(64), 285(63), 311 sh(48); $\lambda_{max}^{0.1NHCl}$ 214(60), 285(59), 311 sh(45); $\lambda_{max}^{0.1N}$ NaOH 227(54), 260(64), 295(57), 348(25);
(c) Infrared absorption spectrum, as shown in FIG. 2 (KBr disk);
(d) Proton magnetic resonance spectrum, as shown in FIG. 3 ($D_2O$);
(e) Carbon-13 NMR spectrum, as shown in FIG. 4 (DMSO-$d_6$); and
(f) Optical rotation: $[\alpha]_D^{25} + 85\% \pm 2°$ (concentration about 0.5%, water).

It is believed that the ash results from sodium.

BRIEF DESCRIPTION OF THE DRAWINGS

FIG. 3 represents the proton magnetic resonance spectrum of antibiotic LL-C19004 ($D_2O$).

FIG. 4 represents the Carbon-13 NMR spectrum of antibiotic LL-C19004 (DMSO-$d_6$).

DETAILED DESCRIPTION OF THE INVENTION

Figure 1:
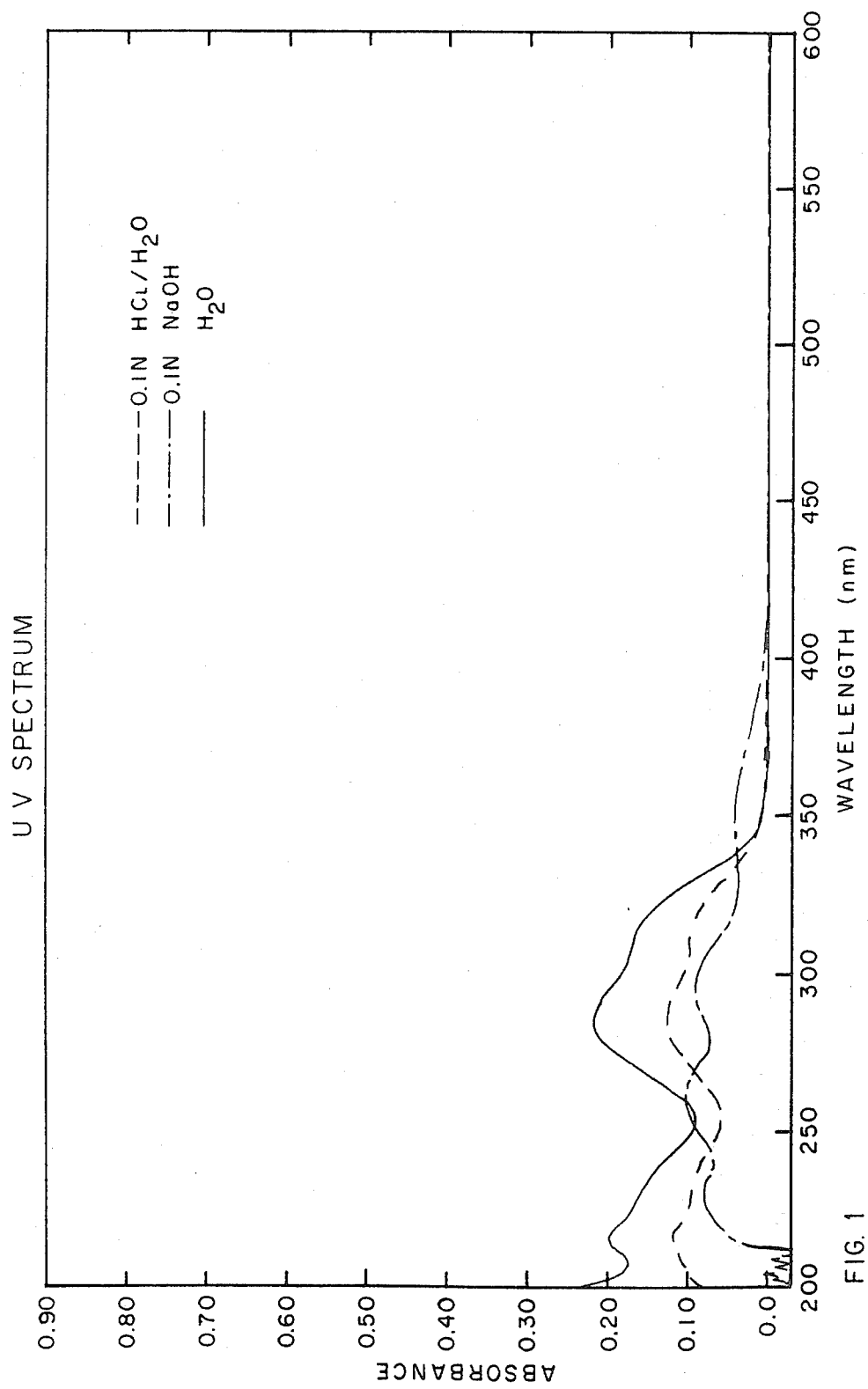
FIG. 1 represents the ultraviolet absorption spectra of antibiotic LL-C19004 (100 mcg/ml).

Culture LL-C19004, which produces the novel antibacterial agent LL-C19004, is a natural selection isolate of a culture isolated from a soil sample collected in Puerto Llano, Spain. The culture was taxonomically characterized and identified as a new species of the genus Saccharothrix, to be known as *Saccharothrix espanaensis* Labeda, sp. nov.

This new species is maintained in the culture collection of the Medical Research Division, American Cyanamid Company, Pearl River, N.Y. as culture number LL-C19004. A viable culture of this new microorganism has been deposited with the ARS Culture Collections, Fermentation Laboratory, Northern Regional Research Center, U.S. Department of Agriculture, 1815 North University Street, Peoria, Ill. 61604, and has been added to its permanent collection. It has been assigned by such depository the strain designation NRRL 15764. Access to such culture, under strain designation NRRL 15764, during pendency of the instant application shall be available to one deterined by the Commissioner of Patents and Trademarks to be entitled thereto under 37 C.F.R. §1.14 and 35 U.S.C. §122, and all restrictions on availability to the public of such culture will be irrevocably removed upon grant of a patent on the instant application.

Observations were made of the cultural, physiological and morphological features of culture LL-C19004 using methods detailed by Shirling, E. B. and D. Gottlieb, Methods for Characterization of Streptomyces Species, Internat. J. Syst. Bacteriol., 16, 313–340 (1966); and Gordon, R. E., et. al., Internat. J. Syst. Bacteriol., 24, 54–63 (1974). Media used in the study were selected from those recommended by Pridham, T. G., et al., A Selection of Media for Maintainance and Taxonomic Study of Streptomycetes. Antibiotics Ann., pp. 947–953, 1956/57; Gauze, G. T., et al., Problems in the Classification of Antagonistic Actinomycetes. State Publishing House for Medical Literature, Medgiz, Moscow, 1957; and Gordon, R. E., Ecology of Soil Bacteria. T. G. R. Gray and B. Parkinson, Eds., Liverpool Univ. Press, 1967 for the Taxonomic Study of Actinomycetes and Soil Bacteria. Chemical composition of the cell walls of the culture was determined using the method of Lechevalier, H. A., et al., Chemical Composition as a Criterion in the Classification of Actinomycetes. Adv. Appl. Microbiol., 14, 47–72 (1971). Phospholipid patterns were determined using the method of Lechevalier, M. P., et al., Chemotaxonomy of Aerobic Actinomycetes: Phospholipid Composition. Biochem. Syst. Ecol., 5, 249–260 (1977). Acid production from carbohydrates was determined by the method of Gordon, et al., (vide supra). Carbohydrate utilization was determined by the method of Pridham, T. G. and D. Gottlieb, The Utilization of Carbon Compounds by Some Actinomycetales as an Aid for Species Determination. J. Bacteriol., 56, 107–114 (1948). Details are recorded in Tables I–VI and a general description of the culture is given below. Underscored descriptive colors are taken from Kelly, K. L. and D. B. Judd, Color. Universal Language and Dictionary of Names. Nat. Bur. Stand. (U.S.), Spec. Publ. 440, 1976, Washington, D.C., and the accompanying Inter-Society Color Council, National Bureau of Standards Centroid Color Charts.

MICROMORPHOLOGY

Spores are formed in very short straight chains on rudimentary aerial sporophores. They may also result from fragmentation of vegetative mycelia. The spores are ovoid in shape, about 0.6 to 0.8 micron by about 1.0 to 1.2 micron and have a substantially smooth surface.

CELL WALL COMPOSITION

Whole cell hydrolysates of this culture contain the meso-isomer of diaminopimelic acid and mannose and galactose as the characteristic sugars. The phospholipid pattern was found to be characteristic for Type PIV, with glucosamine-containing phospholipids as the significant phospholipid type. This chemotaxonomic pattern of cell wall composition, whole cell sugar and phospholipid pattern is characteristic of the genus Saccharothrix.

AMOUNT OF GROWTH

Good growth observed on asparagine-dextrose agar, Bennett's agar, NZ-amine-starch-glucose agar (ATCC Medium 172), tomato paste-oatmeal agar and yeast extract-malt extract agar; moderate growth observed on Benedict's agar, calcium malate agar, inorganic salts-starch agar and oatmeal agar; poor growth observed on Gauze No. 1 agar.

VEGETATIVE MYCELIUM

On medium where good growth occurred, the vegetative mycelium was observed to be flat and waxy and generally yellow to orange-yellow to yellowish brown shades in color.

AERIAL MYCELIUM AND SPORE COLOR

Aerial mycelia absent on most media; very sparse white mycelia when present.

SOLUBLE PIGMENTS

Absent on most media; yellowish pigment on glycerol asparagine agar and inorganic salts-starch agar; brownish pigments on asparagine dextrose agar, NZ-amine-starch-glucose agar, oatmeal agar, tomato paste-oatmeal agar; reddish-brown pigment on yeast extract-malt extract agar.

PHYSIOLOGICAL REACTIONS

No melanin pigments on peptone-iron agar and tyrosine agar (ISP-7); strong peptonization of litmus milk; no proteolysis of nutrient gelatin; weak to no reduction of nitrate; no hydrolysis of tyrosine or xanthine; strong hydrolysis of adenine and hypoxanthine; no decomposition of urea; strong hydrolysis of esculin. Good utilization of fructose, glucose, mannose, sucrose and trehalose; moderate utilization of galactose, glycerol and maltose; poor utilization of salicin; no utilization of adonitol, arabinose, dulcitol, inositol, lactose, mannitol, melezitose, melibiose, raffinose, rhamnose, sorbitol and xylose was observed. Good acid production from fructose, galactose, glucose, glycerol, maltose, mannose, sucrose, trehalose and xylose; no acid produced from adonitol, arabinose, inositol, lactose, mannitol, melezitose, melibiose, raffinose, rhamnose, salicin and sorbitol. Utilization of organic acids by the method of Gordon, et al., (vide supra): utilization of lactate and malate; no utilization of benzoate, citrate, mucate and oxalate. Poor growth at 4° C. and 45° C., moderate growth at 32° C. and 37° C., and good growth at 28° C.

The biochemical composition pattern for culture, meso-diaminopimelic acid, mannose and galactose, and phospholipid pattern-type PIV, absolutely identifies it as a member of the genus Saccharothrix. This culture differs from the type species *Saccharothrix australiensis* NRRL 11239 in several ways. Culture LL-C19004 does not hydrolyze tyrosine or make melanin soluble pigments, although it does hydrolyze adenine, which is not hydrolyzed by the type strain. Another major difference between these strains is the inability of the type strain to grow on the ISP carbohydrate test medium due to its inability to utilize ammonium as a nitrogen source. Culture LL-C19004 is able to use at least nine different carbohydrates with this basal medium. The gross colonial appearance of these two strains is also different, with *S. australiense* having brown to yellowish brown vegetative mycelium and LL-C19004 having mycelia with orange-yellow shades on the same media. In the light of the significant differences between these two cultures, culture LL-C19004 is designated as a new species to be known as *Saccharothrix espanaensis* Labeda, being named for the collection site (country) of the soil sample from which the culture was isolated.

TABLE I

| Medium | Amount of Growth | Description of Colonial Growth | Soluble Pigments |
|---|---|---|---|
| Asparagine Dextrose Agar | Good | Flat waxy growth, 73. pale orange yellow to 75. deep yellowish brown | Brownish |
| Benedict's Agar | Moderate | Flat waxy growth, 70. light orange yellow to 71. moderate orange yellow | None |
| Bennett's Agar | Good to moderate | Flat waxy growth, 76. light yellowish brown to 77. moderate yellowish brown | None |
| Calcium Malate | Moderate | Flat waxy growth, 67. brilliant orange yellow; sparse white aerial mycelia | None |
| Guaze No. 1 Agar | Poor | Flat colorless colonies with a trace of white aerial mycelia | None |
| Glycerol Asparagine Agar | Moderate | Flat waxy growth, 73. pale orange yellow to 76. light yellowish brown; sparse white aerial mycelia | Yellowish |
| Glycerol Casein Agar | Moderate | Flat waxy growth, 90. grayish yellow; a trace of white aerial mycelia | None |
| Hickey-Tresner Agar | Moderate | Flat waxy growth, 79. light grayish yellow brown | None |
| Inorganic Salts-Starch Agar | Moderate | Flat waxy growth, 90. grayish yellow to 74. strong yellowish brown; trace white aerial mycelia | Yellow |
| NZ—amine Starch Glucose Agar | Good | Plicate ridged growth, 77. moderate yellowish brown to 75. deep yellowish brown | Brown |
| Oatmeal Agar | Moderate | Flat waxy growth, 79. light grayish yellow brown; white aerial mycelia | Brownish |
| Tomato Paste- | Good | Plicate waxy growth, 86. light | Brown |

TABLE I-continued

Cultural Characteristics of *Saccharothrix espanaensis* LL-C19004

| Medium | Amount of Growth | Description of Colonial Growth | Soluble Pigments |
|---|---|---|---|
| Oatmeal Agar | | yellow to 77. moderate yellowish brown; no aerial mycelia | |
| Yeast Extract-Malt Extract Agar | Good | Plicate waxy growth, 90. grayish yellow to 78. dark yellowish brown | Reddish brown |

TABLE II

Micromorphology of *Saccharothrix espanaesis* LL-C19004

| Medium | Aerial Mycelium and/or Sporiferous Structures | Spore Shape | Spore Size | Spore Surface |
|---|---|---|---|---|
| Tap water-crude agar | Rudimentary aerial mycelia, fragmenting into ovoid "spores"; vegetative mycelia also appear to fragment | ovoid | 0.6–0.8 micron × 1.0–1.2 micron | smooth |

TABLE III

Physiological Reactions of *Saccharothrix espanaensis* LL-C19004

| Medium | Incubation (Days) | Amount of Growth | Physiological Reaction |
|---|---|---|---|
| Peptone-Iron Agar | 7 | Good | Slight browning |
| | 14 | Good | Slight browning |
| Tyrosine Agar (ISP-7) | 7 | Good | Slight browning |
| | 14 | Good | Yellow pigment |
| Litmus Milk | 14 | Good | Strong peptonization |
| | 28 | Good | Strong peptonization |
| Nutrient Gelatin | 14 | Good | No proteolysis |
| | 28 | Good | No proteolysis |
| Nitrate Broth | 14 | Good | No reduction |
| | 28 | Good | Weak reduction |
| Adenine Agar | 14 | Good | Hydrolysis |
| | 28 | Good | Strong hydrolysis |
| Hypoxanthine Agar | 14 | Good | Hydrolysis |
| | 28 | Good | Strong hydrolysis |
| Tyrosine Agar | 14 | Good | No hydrolysis |
| | 28 | Good | No hydrolysis |
| Xanthine Agar | 14 | Good | No hydrolysis |
| | 28 | Good | No hydrolysis |
| Urea Broth | 28 | Good | No decomposition |
| Esculin Broth | 14 | Good | Strong hydrolysis |
| NZ—Amine with Soluble Starch and Glucose Agar (ATCC Med. No. 172) | 5 | Poor or no growth at about 4° C. and about 45° C.; moderate growth at about 32° C. and about 37° C.; good growth at 28° C. | |

TABLE IV

Carbon Source Utilization of *Saccharothrix espanaensis* LL-C19004 on ISP-9 Carbohydrate Utilization Medium (Incubation: 28 days, about 28° C.)

| Carbon Source | Utilization |
|---|---|
| Adonitol | 0 |
| l-Arabinose | 0 |
| Dulcitol | 0 |
| Fructose | 3 |
| d-Galactose | 2 |
| d-Glucose | 3 |
| Glycerol | 2 |
| i-Inositol | 0 |
| Lactose | 0 |
| Maltose | 2 |
| d-Mannitol | 0 |
| d-Mannose | 3 |
| d-Melezitose | 0 |
| d-Melibiose | 0 |
| d-Raffinose | 0 |
| l-Rhamnose | 0 |
| Salicin | 1 |
| Sorbitol | 0 |
| Sucrose | 3 |
| d-Trehalose | 3 |
| d-Xylose | 0 |
| Negative control | 0 |

3 = Good utilization
2 = Fair utilization
1 = Poor utilization
0 = No utilization

TABLE V

Acid Production from Various Carbohydrates by *Saccharothrix espanaensis* LL-C19004 on Gordon's Basal Inorganic Nitrogen Medium Incubation: 28 days, about 28° C.

| Carbon Source | Acid Production | |
|---|---|---|
| | 7 Days | 28 Days |
| Adonitol | − | − |
| l-Arabinose | − | − |
| Fructose | +/− | + |
| d-Galactose | − | + |
| d-Glucose | + | + |
| Glycerol | + | + |
| i-Inositol | − | − |
| Lactose | − | − |
| Maltose | + | + |
| d-Mannitol | − | − |
| d-Mannose | +/31 | + |
| d-Melezitose | − | − |
| d-Melibiose | − | − |
| d-Raffinose | − | − |
| l-Rhamnose | − | − |
| Salicin | − | − |
| Sorbitol | − | − |
| Sucrose | +/− | + |
| d-Trehalose | +/− | + |
| d-Xylose | − | + |
| Negative control | − | − |

+ = good production
− = no production
+/− = some production

TABLE VI

Utilization of Organic Acids by *Saccharothrix espanaensis* LL-C19004 on Gordon's Modification of Koser's Basal Agar (Koser's Citrate Agar)
Incubation: 28 days, about 28° C.

| Carbon Source | Utilization |
| --- | --- |
| Benzoate | − |
| Citrate | − |
| Lactate | + |
| Malate | + |
| Mucic Acid | − |
| Oxalate | − |

\+ = yes
− = no

It is to be understood that for the production of this new antibacterial agent the present invention is not limited to this particular organism or to organisms fully answering the above growth and microscopic characteristics which are given for illustrative purposes only. In fact, it is desired and intended to include the use of mutants produced from this organism by various means such as exposure to X-radiation, ultraviolet radiation, N'-methyl-N'-nitro-N-nitrosoguanidine, actinophages and the like.

The in vitro antibacterial effects of antibiotic LL-C19004 were determined by standard agar dilution methods against clinical isolates obtained from medical centers representing various geographical areas in the United States. The inoculum of each culture was approximately 1 to $5 \times 10^4$ colony forming units applied with the Steers multiple inocula replicator to plates containing the antibiotic in Mueller-Hinton agar. The agar was supplemented with about 5% sheep blood where required for the growth of the organism. Wilkins-Chalgren agar was used for testing the anaerobic bacteria. The results are presented in Table VII.

TABLE VII

In vitro Antibacterial Spectrum of Antibiotic LL-C19004

| Organisms (No. of Strains Tested) | | Minimal Inhibitory Concentration mcg/ml Range | Concentration mcg/ml Required to Inhibit 90% of Strains Tested |
| --- | --- | --- | --- |
| Gram Positive | | | |
| *Staphylococcus aureus* | (61) | 0.12–2 | 0.5 |
| Streptococcus spp. β-hemolytic | (11) | 1–2 | 2 |
| *Streptococcus pneumoniae* | (11) | 0.5–2 | 2 |
| *Streptococcus enterococcus* | (30) | 0.25–8 | 4 |
| Gram Negative | | | |
| *Neisseria gonorrhoeae* | (11) | 0.25–1 | 1 |
| *Haemophilus influenzae* | (13) | 1–4 | 4 |
| *Escherichia coli* | (15) | 16–32 | 32 |
| Klebsiella spp. | (15) | 16–32 | 32 |
| Enterobacter spp. | (15) | 4–64 | 64 |
| Serratia spp. | (15) | 32–>128 | 32 |
| Proteus (indole+) spp. | (17) | 16–>128 | >128 |
| Acinetobacter spp. | (15) | 4–16 | 16 |
| *Pseudomonas aeruginosa* | (15) | 32–128 | 128 |
| Anaerobes | | | |
| *Bacteroides fragilis* | (15) | >128 | >128 |

The in vivo activity of antibiotic LL-C19004 was assessed in female mice, strain CD-1, weighing 20±2 g each, infected intraperitoneally with sufficient bacterial cells suspended in broth or about 5% mucin to kill approximately 95 to 100% of untreated mice within about 48 hours. Antibiotic LL-C19004 was administered in single subcutaneous doses about ½ hour after infection. Seven day survival ratios from 3 to 4 separate tests were pooled for the determination of the median effective dose ($ED_{50}$) by probit analysis. The results are summarized in Table VIII.

TABLE VIII

In Vivo Activity of Antibiotic LL-C19004

| Infection | Median Effective Dose mg/kg (95% Confidence Limits) |
| --- | --- |
| *Staphylococcus aureus* Smith | 0.06 (0.04–0.07) |
| *Staphylococcus aureus* Rose | 2.6 (1.9–3.5) |
| *Streptococcus pyogenes* C203 | 0.90 (0.70–1.1) |
| *Streptococcus pneumoniae* SV1 | 0.85 (0.70–1.1) |
| *Escherichia coli* No. 311 | >8 |
| *Klebsiella pneumoniae* AD | >8 |

GENERAL FERMENTATION CONDITIONS

Cultivation of *Saccharothrix espanaensis* LL-C19004 may be carried out in a wide variety of liquid culture media. Media which are useful for the production of antibiotic LL-C19004 include an assimilable source of carbon, such as starch, sugar, molasses, glycerol, etc.; an assimilable source of nitrogen such as protein, protein hydrolysate, polypeptides, amino acids, cornsteep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the medium. Aeration in tanks and bottles is supplied by forcing sterile air through or onto the surface of the fermenting medium. Agitation is provided by a mechanical impeller. An antifoam agent may be added as needed. The growth of the organism is usually conducted at about 24°–37° C., preferably at about 28° C.

GENERAL PROCEDURE FOR ISOLATION OF ANTIBIOTIC L-C19004

Antibiotic LL-C19004 is recovered from the fermentation filtrate by adsorption on a column of macroreticular resin such as Amberlite ® IRC(NH$_4$+) and elution from the column with dilute alkali such as 2N ammonium hydroxide. The active fractions are further purified on a column of CM Sephadex ® (NH$_4$+) by elution with a water-1.5M ammonium hydroxide gradient.

Production of the antibiotic complex during the fermentation processing and purification steps can be followed by testing samples against an organism known to be sensitive to antibiotic LL-C19004. A turbidimetric bioassay procedure using *Staphylococcus aureus* ATCC 6538P grown in antibiotic medium No. 3 (Difco) and the Elanco Autoturb instrument is useful for this purpose.

EXAMPLE 1

Inoculum Preparation

A typical medium used to grow the primary inoculum was prepared according to the following formula:

| Dextrose | about 1.0% |
|---|---|
| Dextrin | about 2.0% |
| Yeast extract | about 0.5% |
| NZ Amine A | about 0.5% |
| Calcium carbonate | about 0.1% |
| Water qs | 100% |

This medium was sterilized. An approximately 100 ml portion of this medium, in a 500 ml flask, was inoculated with mycelial scrapings from an agar slant of the culture *Saccharothrix espanaensis* LL-C19004. The medium was then placed on a rotary shaker and agitated vigorously for approximately 72 hours at about 28° C., providing primary inoculum.

An approximate 100 ml portion of this primary inoculum was then used to inoculate about one liter of medium of the same formulation which was then incubated at about 28° C. with aeration for approximately 48 hours, providing secondary inoculum.

Approximately one liter portion of this secondary inoculum was then used to inoculate about 26 liters of medium of the same formulation in a tank, which was incubated at about 28° C. with agitation by an impeller driven at about 500 rpm, a sterile air flow of about 30 liters per minute and the addition of about 75 ml of a defoaming agent for about 48 hours, providing tertiary inoculum.

EXAMPLE 2

Fermentation

A fermentation medium was prepared according to the following formulation:

| Dextrin | about 3.0% |
|---|---|
| Molasses | about 2.0% |
| Soya peptone | about 0.75% |
| Yeast extract | about 0.25% |
| Water qs | 100% |

An approximate 245 liter portion of this medium in a tank was adjusted to pH 8.5–8.6, sterilized and then inoculated with about 30 liters of tertiary inoculum prepared as described in Example 1. Aeration was supplied at the rate of about 150 liters of sterile air per minute and agitation was supplied by an impeller driven at about 175 rpm. The temperature was maintained at about 28° C., silicone antifoam agent was added as required, and the fermentation was monitored for production of antibiotic LL-C19004 by antibacterial activity, TLC and HPLC analyses. The fermentation was terminated after about 80 hours, at which time the mash was harvested.

EXAMPLE 3

Isolation of Antibiotic LL-C19004

The whole mash from three fermentations, conducted as described in Example 2, were pooled providing about 820 liters of mash. An approximate 41 kg portion of diatomaceous earth was added and this mixture was filtered, and the cake was washed with about 123 liters of water. The filtrate and wash were combined providing about 900 liters of solution at about pH 7.6 This solution was then passed, at a flow rate of 575–625 ml/minute, through a column containing a 14 liter bed volume of Amberlite ® IRC 50($NH_4^+$) ion exchange resin. The column was next washed with about 40 liters of water at a flow rate of 515–625 ml/minute and was then eluted with about 60 liters of 2N ammonium hydroxide, at a flow rate of 575–625 ml/minute, collecting fractions of about 6 liters each. Fraction number two was concentrated to about 2 liters and then freeze-dried, providing about 114 g of solid.

An about 5.0 g portion of the above solid was mixed with about 25 ml of water, adjusted to about pH 7.0 with hydrochloric acid and placed on a 3×45 cm column of CM Sephadex ® ($NH_4^+$). Pump pressure was applied to force the solution down the column. The column was eluted first with about 250 ml of water and then with a linear gradient of water-1.5M ammonium hydroxide for about 2 hours as about 5 ml fractions were collected. Pooling of fractions was based on an autoturb assay with *Staphylococcus aureus* 209P, ATCC No. 6538P. Fractions 108–119 were combined and freeze-dried, giving about 1.25 g of substantially pure antibiotic LL-C19004 as a white powder.

ISOLATION OF THE CHROMOPHORE OF LL-C19004

The procedure used to isolate the the chromophore of LL-C19004 is essentially the same reported by R. L. Mann and D. O. Woolf for the isolation of 3,4-dihydroxy-α-methylcinnamic acid from hydromycin A (JACS 79:120–126, 1957).

A solution of LL-C19004 (6 g) in 250 ml. of 10% sodium hydroxide in the presence of 4 g of zinc was heated under reflux in a nitrogen atmosphere for 16 hr. The hydrolysate was acidified to pH 2.0 with concentrated sulfuric acid and extracted twice with 200 ml portions of ether. The combined ether solutions were extracted twice with 100 ml. portions of 5% sodium bicarbonate solution. The alkaline solution was acidified to pH 2.0 with 5N sulfuric acid and the ether extraction repeated. The ether solution was dried over sodium sulfate, benzene added and the mixture concentrated on a rotary evaporator to a small volume. A small volume of hexane was added and the organic layer concentrated and dried to give 122 mg. of an orange solid. Ninety mg of the orange solid was dissolved in methanol and spotted on silica gel $F_{254}$ glass-backed plates (20×20 cm) followed by development in the solvent system benzene, methanol, glacial acetic acid (45:8:4). Using a combination of visible color, UV quenching under a short wave hand lamp and direct comparison with an authentic sample of 3,4-dihydroxycinnamic acid, it was possible to locate the LL-C19004 chromophore at Rf 0.10. The area of Rf 0.10 was removed from the surface of the TLC, placed in a glass Pasteur pipette fitted with glass wool and eluted with methanol. The eluate was collected in a tared vial and taken to dryness under a stream of nitrogen. The amount recovered was 12.86 mg of orange solid.

Chemical data accumulated on 12.86 mg of TLC product include IR, UV and proton NMR. All the data, in addition to TLC results using ferric chloride spray reagent, identified this product as 3,4-dihydroxycinnamic acid.

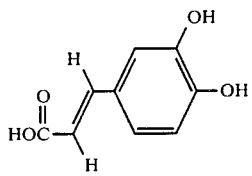

The $^{13}$C NMR spectrum of the intact antibiotic (FIG. 4) in DMSO-d$_6$ had peaks at 164.9, 147.1, 146.7, 138.5, 130.1, 120.5, 119.8, 116.0 and 114.0 ppm attributed to this moiety.

METHANOLYSIS OF N-ACETYLATED COMPLEX

N-acetylated antibiotic LL-C19004 (4.0 g) was refluxed in dry methanol containing 5% by weight HCl gas for 4 hr. After the solution had cooled to room temperature, it was neutralized by the batchwise addition of solid (Ag)$_2$CO$_3$(15 g) with stirring. The resulting suspension was filtered and the filtrate was evaporated in vacuo to a black syrup. This syrup was partitioned between water (120 ml) and ethyl acetate (100 ml) in a separatory funnel. Upon evaporation the ethyl acetate layer yielded 300 mg of residue (6550C-115C) which contained an aminosugar. The aqueous layer was also evaporated in vacuo to a syrup (6550C-115B) which upon further processing yielded derivatives of neutral sugars and a disaccharide.

ACETYLATION OF WATER SOLUBLE FRACTION

The syrup obtained above (6550C-115B) was dissolved in pyridine (10 ml) and acetic anhydride (6 ml) was added. The solution was heated at 50° for 17 hr. The reagents were evaporated in vacuo at 40° to yield a crude product weighing 5.8 gm.

SILICA GEL CHROMATOGRAPHY OF ACETYLATED WATER SOLUBLE FRACTION

The crude acetylated product (5.8 g) was chromatographed on a silica gel column (Woelm TSC, 2.5×72 cm) developed with chloroform. After a forerun of 200 ml, 5 ml fractions were collected. Fractions were combined as follows on the basis of TLC analysis:

| Fr. Combined | Designation | Weight (g) |
|---|---|---|
| 2–14 | 6550C-117A | 0.50 |
| 15–40 | 117B | 1.08 |
| 41–50 | 117C | .32 |
| 51–66 | 17D | .69 |
| 67–90 | 117E | 1.00 |

CHROMATOGRAPHIC SEPARATION OF 6550C-117B

The bulk of fraction 6550C-117B was chromatographed on a silica gel column (Woelm TSC, 200 g, 2.5×85 cm) developed with ethyl acetate:hexane (1:4) at 1.0 ml/min. Fractions were collected every five minutes. Fractions were combined based upon TLC analysis as follows:

| Fr. Combined | Designation | Weight (mg) |
|---|---|---|
| 155–162 | 6550C-119C(1) | 60 |
| 235–279 | 6550C-119E(2) | 200 |

Washing the column with 340 ml of mobile phase gave one final fraction designated 6550C-119F (3) 20 mg.

CHROMATOGRAPHIC SEPARATION OF 6550C-117E

The bulk of fraction 6550C-117E was chromatographed on a silica gel column (Woelm TSC, 200 g, 2.5×80 cm) developed with toluene:ethyl acetate:ethanol (18:6:1) at a rate of 1.5 ml/min. Fractions were collected every fifteen minutes. Fractions were combined based upon TLC analysis as follows:

| Fr. Combined | Designation | Weight (mg) |
|---|---|---|
| 32–36 | 6550C-123A(7) | 400 |
| 40–47 | 6550C-123B | 300 |

SILICA GEL CHROMATOGRAPHY OF ETHYL ACETATE SOLUBLE FRACTION 6550C-115C

Ethyl acetate soluble part of the methanolysis product 6550C-115C (150 mg) was chromatographed on a silica gel column (Woelm TSC, 100 g, 2.5×35 cm) in methanol:methyl chloride (1:40) at a rate of 1.5 ml/min. Fractions were collected every 15 minutes, fractions 26 and 27 were combined.

| Fr. No. | Designation | Weight (mg) |
|---|---|---|
| 25 | 6550C-125A(4) | 20 |
| 26 & 27 | 6550C-125C | 70 |
| 28 | 6550C-125B(5) | 10 |

IDENTIFICATION OF SUGARS AND DISACCHARIDE

Compound 6550C-119C (1) (from factions 115–162) (60 mg) was identified as methyl-2,3,4-tri-O-acetyl-6-deoxy-α-mannopyranoside. The following structure was assigned, based upon spectroscopic data:

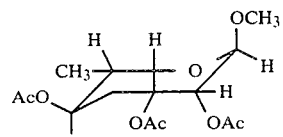

Compound 6550C-119E (2) (from fractions 235–279) (200 mg) was identified as methyl-2,3,4-tri-O-acetyl-6-deoxy-α-galactopyranoside. The following structure was assigned based upon spectroscopic data:

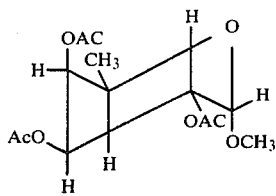

Compound 6550C-125A (4) (from fraction 25) (20 mg) was identified as methyl-3-acetamido-2,3,6-trideoxy-3-C-methyl-α-D-ribo-hexopyranoside. The following structure was assigned, based upon spectroscopic data:

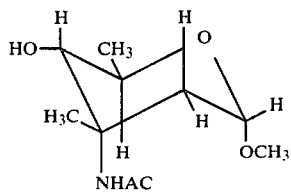

Compound 6550C-123A (7), a disacchauride (from fractions 32-36) (400 mg), was assigned the following structure based upon spectroscopic data:

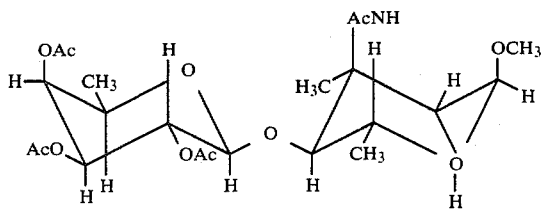

Figure 2:
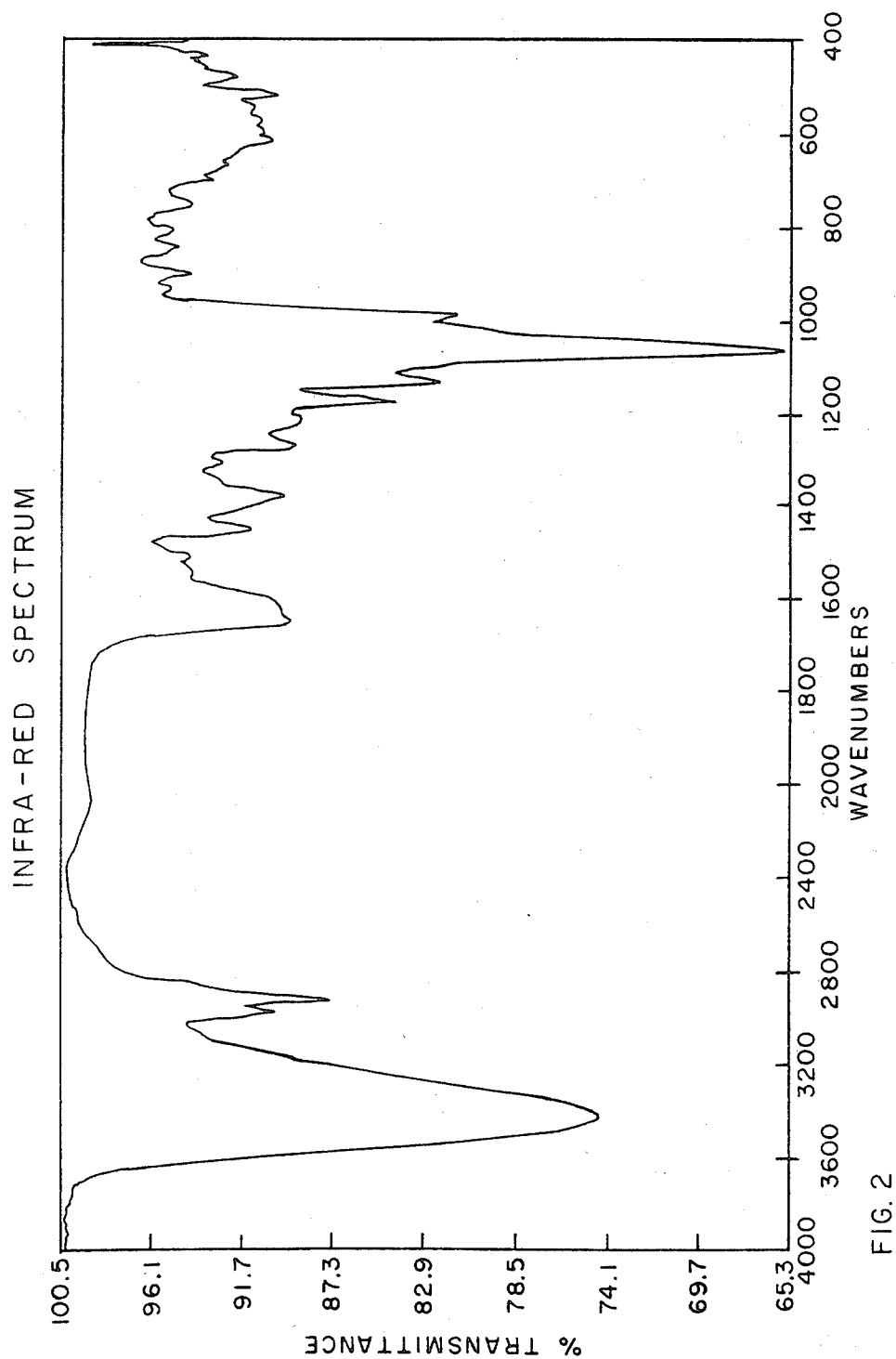
FIG. 2 represents the infrared absorption spectrum of antibiotic LL-C19004 (K Br disk).

What is claimed is:

1. Antibiotic LL-C19004, which:
   (a) has an approximate elemental analysis: C, 45.14; H, 6.48; N, 4.16; S, 1.70; O, 34.90; and ash, 7.1;
   (b) has ultraviolet absorption spectra as shown in FIG. 1;
   (c) has an infrared absorption spectrum as shown in FIG. 2;
   (d) has a proton magnetic resonance spectrum as shown in FIG. 3;
   (e) has a carbon-13 NMR spectrum as shown in FIG. 4; and
   (f) has an optical rotation $[\alpha]_D^{25} = -85° \pm 2°$(c 0.5%, water).

2. A method of treating bacterial infections in warm-blooded animals which comprises administering by injection to said animals an antibacterially effective amount of LL-C19004 as defined in claim 1.

3. A process for producing antibiotic LL-C19004 as defined in claim 1 which comprises aerobically fermenting the microorganism *Saccharothrix espanaensis* (NRRL 15764) or mutants thereof which also produce antibiotic LL-C19004 as defined in claim 1 in a liquid medium containing assimilable sources of carbon, nitrogen and inorganic salts, until substantial antibiotic activity is imparted to said medium and then recovering the antibiotic therefrom.

4. The process as recited in claim 3 for producing antibiotic LL-C19004 as defined in claim 1 which comprises aerobically fermenting a liquid medium containing assimilable sources of carbon, nitrogen and inorganic salts, which medium has been innoculated with a viable culture of the microorganism *Saccharothrix espanaensis* (NRRL 15764) or mutants thereof which also produce antibiotic LL-C19004 as defined in claim 1 maintaining said fermentation culture at a temperature of about 24°-32° C. for a period of approximately 72-150 hours, harvesting the mash and extracting the antibiotic.

* * * * *